US009557583B2

(12) United States Patent
Farache

(10) Patent No.: US 9,557,583 B2
(45) Date of Patent: Jan. 31, 2017

(54) SYSTEM, METHOD AND DEVICE FOR MEASURING PUPILLARY DISTANCES

(71) Applicant: Fortunato Farache, Doral, FL (US)

(72) Inventor: Fortunato Farache, Doral, FL (US)

(73) Assignee: Fortunato Farache, Weston, FL (US)

( * ) Notice: Subject to any disclaimer, the term of this patent is extended or adjusted under 35 U.S.C. 154(b) by 0 days.

(21) Appl. No.: 14/744,545

(22) Filed: Jun. 19, 2015

(65) Prior Publication Data

US 2016/0202499 A1  Jul. 14, 2016

Related U.S. Application Data

(63) Continuation-in-part of application No. 14/593,908, filed on Jan. 9, 2015, now Pat. No. 9,091,867.

(60) Provisional application No. 62/148,720, filed on Apr. 16, 2015, provisional application No. 62/147,583, filed on Apr. 15, 2015.

(51) Int. Cl.
*G02C 13/00* (2006.01)
*A61B 3/00* (2006.01)
*A61B 3/11* (2006.01)

(52) U.S. Cl.
CPC ........... *G02C 13/005* (2013.01); *A61B 3/0025* (2013.01); *A61B 3/111* (2013.01)

(58) Field of Classification Search
USPC .......................... 351/200–246; 345/629, 632
See application file for complete search history.

(56) References Cited

U.S. PATENT DOCUMENTS 7,950,800 B2 * 5/2011 Nauche ................ G02C 13/005
351/204
8,556,420 B2 * 10/2013 Sayag .................. G02C 13/003
351/204

* cited by examiner

*Primary Examiner* — Mohammed Hasan
(74) *Attorney, Agent, or Firm* — Daniel Finnegan

(57) ABSTRACT

A measuring system that embodies a method and a calibration frame for use in measuring pupillary distances is provided. The calibration frame provides true measurements as well as known measurements over a vertical plane co-planar between at least two identified points. The method includes a photographed image of the calibration frame worn by the individual so that using the true and/or known measurements of the calibration frame to compare to their corresponding "apparent" distance measured of the photographed image, the pupillary distances can be determined for providing a prescription lens for a frame desired by the individual. Thereby the measuring of pupillary distances that can take into account relevant position of the person's nose-bridge through a universal calibration frame that can be worn by individuals, and so facilitates online purchases as well as in-store dispensing of prescription frames.

14 Claims, 4 Drawing Sheets

SYSTEM, METHOD AND DEVICE FOR MEASURING PUPILLARY DISTANCES

CROSS-REFERENCE TO RELATED APPLICATION

This application is continuing application claiming the benefit of U.S. patent application Ser. No. 14/593,908, filed 9 Jan. 2015 now U.S. Pat. No. 9,091,867 B2, the contents of which are herein incorporated by reference. This application claims the benefit of priority of U.S. provisional application No. 62/148,720, filed 16 Apr. 2015, the contents of which are herein incorporated by reference; and the benefit of priority of U.S. provisional application No. 62/147,583, filed 15 Apr. 2015, the contents of which are herein incorporated by reference.

BACKGROUND OF THE INVENTION

The present invention relates to pupillary measurements and, more particularly, to a system, method and device for measuring pupillary distance that can take into consideration relevant position of the individual's nose-bridge through a calibration frame, and so facilitating online purchases as well as in-store dispensing of prescription frames.

Traditionally, measuring pupillary distance required an individual to utilize the services of an optician using a ruler or specialized equipment, usually by visiting an optical store, to obtain such measurements. Such measurements include pupillary distances, wherein the pupillary distances are the horizontal distance between each eye-pupil and the center of the frame nose-bridge (always necessary to make eyeglasses).

In-store measurements were the norm because even a small pupillary distance error can make prescription eyeglasses exhibit prismatic behavior, causing squinting, headaches, and dizziness. The importance of aligning an optical lens with the individual's eye pupil is one of the key factors for making prescription eyeglasses successfully.

Recently, methods of measuring pupillary distance have been developed so the individual need not employ the services of an optician—i.e., remote methods. One popular method consists on taking a picture of the individual while placing the back-side of a credit card, a CD/DVD or an object of a commonly known length on his/her chin in order to be able to obtain the scale of the picture and calculate the inter-pupillary distance from the picture. However, this method is not suitable for an individual with an asymmetrical face, as the actual pupillary distances from the nose to their corresponding right and left eyes may differ from the value obtained from a single inter-pupillary measurement.

Another popular remote method consists on having the individual taking his/her own measurements in front of a mirror using a ruler; either with or without the assistance of another person. Since even experienced opticians have difficulty taking their own measurement in a mirror, this method is prone to pupillary measurement error(s) and its associated effects mentioned above.

Yet, another remote method consists on taking a picture of the individual's face; then analyzing the image with the assumption that all human iris have the same diameter-size in order to establish a picture scale and an inter-pupillary distance from the picture; since the size of the human iris varies from person to person with a range of 10.2 to 13 mm, this method is prone to pupillary measurement errors and neither suitable for an individual with an asymmetrical face.

As can be seen, there is a need for a system for measuring pupillary distances that can take into account the actual position of the individual's nose-bridge through employing a calibration frame that can be mass produced for universal application, and so facilitating online purchases as well as in-store dispensing of prescription frames.

SUMMARY OF THE INVENTION

In one aspect of the present invention, a method for measuring pupillary distances that can take into account relevant position of an individual's nose-bridge includes providing a calibration frame with at least one known measurement between two identified points; capturing a photographed image of the calibration frame being comfortably worn by the individual; and determining a scale factor of the photographed image by comparing the at least one known measurement to an apparent distance between the two identified points captured on the photographed image.

In another aspect of the present invention, a system for measuring pupillary distances that can take into account relevant position of the person's nose-bridge includes a calibration frame with at least one known measurement between two identified points; a computer having a user interface; and a program product comprising machine-readable program code for causing, when executed, the computer to perform the following process steps: instructing the user to capture and transmit a photographed image of the calibration frame being comfortably worn by the individual; receiving the photographed image from the user; and determining a scale factor of the photographed image by comparing the at least one known measurement to an apparent distance between the two identified points captured on the photographed image.

In yet another aspect of the present invention, a calibration frame for measuring pupillary distances that can take into account relevant position of the person's nose-bridge includes two eye-frames joined at a nose-bridge, forming a planar front; a strand or a pair of arms pivotably connected to opposing ends of the two eye-frames; and at least two identified points along the planar front having at least one known measurement. In certain embodiments the two eye-frames and the nose-bridge may consist of just one simple element.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a measuring system that embodies a method and a calibration frame for use in measuring pupillary distances. The calibration frame provides true measurements as well as known measurements over a vertical plane co-planar between at least two identified points. The method includes a photographed image of the calibration frame worn by the individual so that using the true and/or known measurements of the calibration frame to compare to their corresponding "apparent" distance measured of the photographed image, the pupillary distances can be determined for providing a prescription lens for a frame desired by the individual. Thereby the measuring of pupillary distances can take into account relevant position of the person's nose-bridge through a universal calibration frame worn by the individual, and so facilitates online purchases as well as in-store dispensing of prescription frames.

Referring to FIGS. 1 through 4, the present invention provides a measuring system that embodies a method 60 and a calibration frame 10 for use in measuring pupillary distance, facilitating online purchase as well as in-store dispensing of prescription eyeglasses.

The measuring system may include at least one computer with a user interface. The computer may include any computer including, but not limited to, a desktop, laptop, and smart device, such as, a tablet, a smart watch, and a smart phone. The computer includes a program product including a machine-readable program code for causing, when executed, the computer to perform steps. The program product may include code, software and/or a relevant software application that can either be loaded onto the computer or accessed by the computer. The loaded code and software may include an application on a smart device. The code and software may be accessed by the computer through the Internet. The computer may access the code and software through its own memory, the internet, extranet, intranet, host server, internet cloud and the like.

Figure 4:
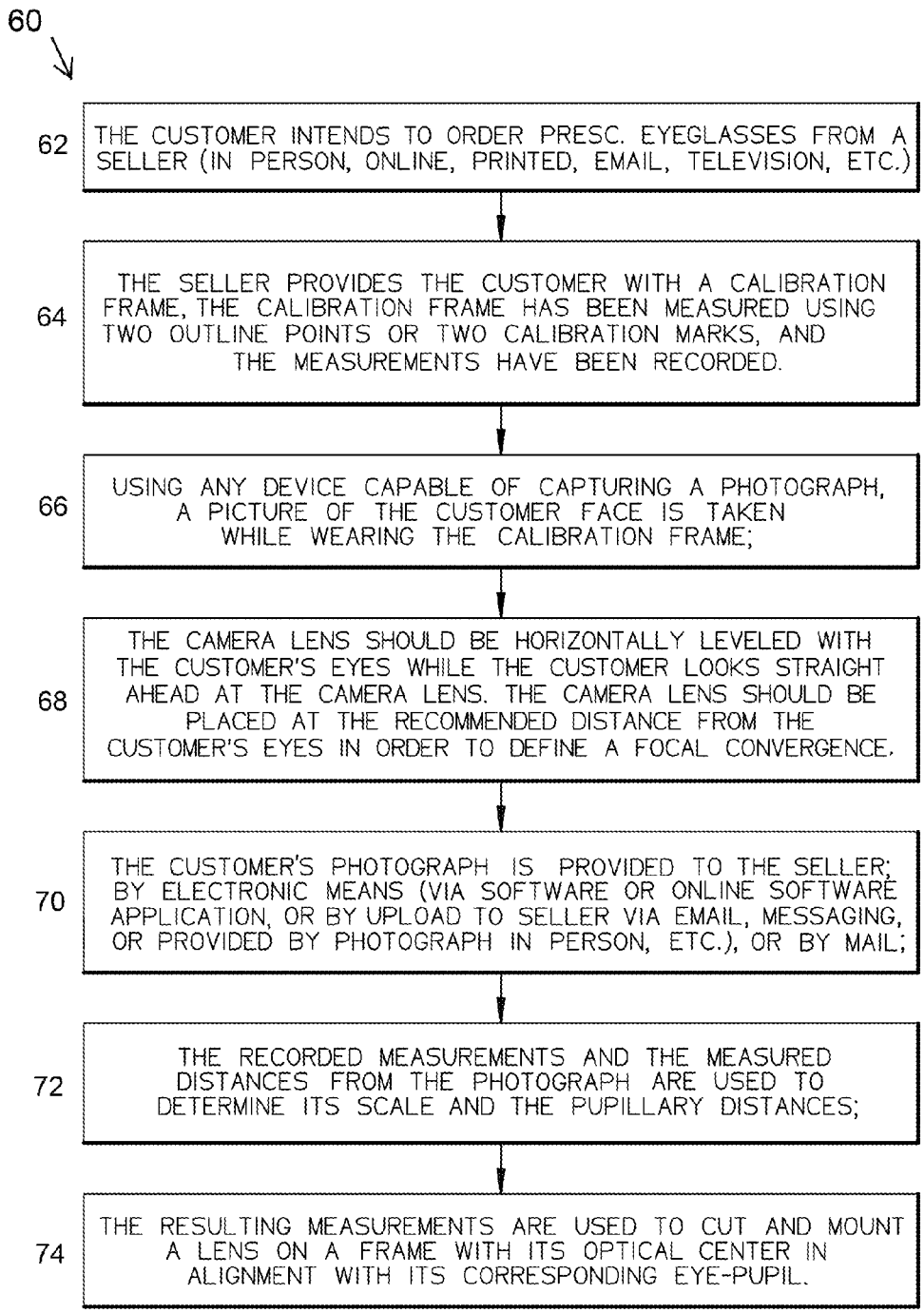
FIG. 4 is a flow chart of an exemplary embodiment of the present invention.

Referring to FIG. 4, the method 60 may include the following steps. The program product may include a relevant code or a software application having machine-readable program code for causing, when executed, the computer to perform the process steps of method 60

In step 62, an individual intends to order a prescription frame, which may include any optical frame designed for housing at least one prescription lens. The order may be made by selecting from a vendor; either in-store, online, through a website, from a catalog or TV, by mail, phone or through the relevant software application. The individual may provide his/her optical prescription to the vendor.

In step 64, the individual is provided with a calibration frame 10. The calibration frame 10 will have at least one known measurement; either (a) a true-size distance of the front of the calibration frame 10 over its vertical (co-planar) plane between selected Outline Points OP1$t$ and OP2$t$, hereinafter DOPt, or (b) a true-size distance between known co-planar Calibration Marks CM1$t$ and CM2$t$, hereinafter DCMt, as illustrated on FIG. 1. OP1$t$, OP2$t$, CM1$t$ and CM2$t$ are known as identified points. Either DOPt or DCMt may be used to determine the true-size of the calibration frame 10. The calibration frame 10 may provide two eye-frames joined at a nose-bridge. In certain embodiments, the calibration frame 10 may be a unitary construction including the two eye-frames and the nose-bridge.

In step 66, the user captures a photographed image 12 by using an imagining device 28 including, but not limited to, a digital camera of a smart-phone, a tablet, a smart watch, a computer device, or electronically connected to the relevant software application. The user is instructed to take the photographed image 12 while the individual is wearing the calibration frame 10 comfortably—as he/she intends to wear his/her eyeglasses normally. The instructions may be provided by the relevant software application. In certain embodiments the user and the individual may be the same person.

In step 68, the instructions may include a certain predetermined distance 30 between a lens 26 of the imaging device 28 and the individual's left and right eyes 32, 34. The instructed predetermined distance 30 may define a co-planar focal convergence point. The instructions may recommend the individual's eyes 32, 34 to be centered and horizontally leveled with the camera lens 26, and also may recommend the individual to look at the camera lens 26 with the head straight (like when driving a car on a straight road) so that the instructed predetermined distance is co-planar with the individual's left and right eye.

In step 70, the user provides the photographed image 12 to the vendor, and/or to a third party. The photographed image 12 may be transmitted electronically via software application or online software application, or uploaded to the seller via online, email, messaging, cloud; etc.; or sent by mail in a physical form.

In step 72, the photographed image 12 is analyzed either by a software application, the vendor, and/or a third party. Already knowing DOPt or DCMt, the scale factor of the image (K) can be sufficiently determined from the relationship between either DOPt or DCMt of the true calibration frame 12 and their corresponding measurement(s) of the apparent calibration frame 14 from the photographed image 12.

$$K=DCMt/DCMp \text{ or } K=DOPt/DOPp$$

Pupillary Distances: With K determined, the photographed image 12 can be used to measure the PDp distance between the centers of both eye-pupils (22, 20), and the PD(OD)p and PD(OS)s distances from the centers of the eye-pupils of the right and left eyes (22, 20) to the center of the nose-bridge; then multiplying by the scale factor, K, to calculate the inter-pupillary distance PD, and the right and left pupillary distances PD(OD) and PD(OS):

$$PD=PDp \times K$$

$$PD(OD)=PD(OD)p \times K$$

$$PD(OS)=PD(OS)p \times K$$

$$PD=PD(OD)+PD(OS)$$

In essence, scaling involves comparing a known distance and an "apparent" (version of the) known distance as captured on the photographed image 12. Moreover, the summation of PD(OD) and PD(OS) can be used to confirm the PDp×K calculation.

Figure 1:
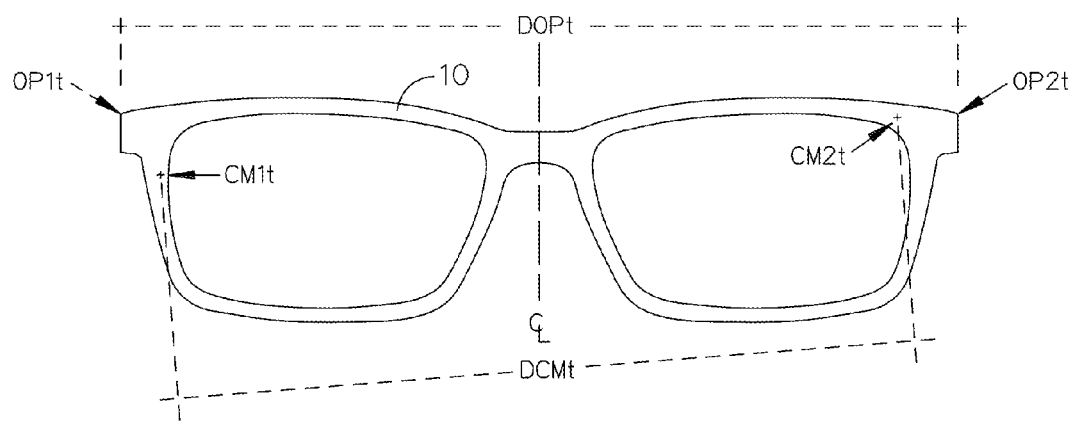
FIG. 1 is a schematic front view of an exemplary embodiment of a calibration frame of the present invention.
Figure 2:
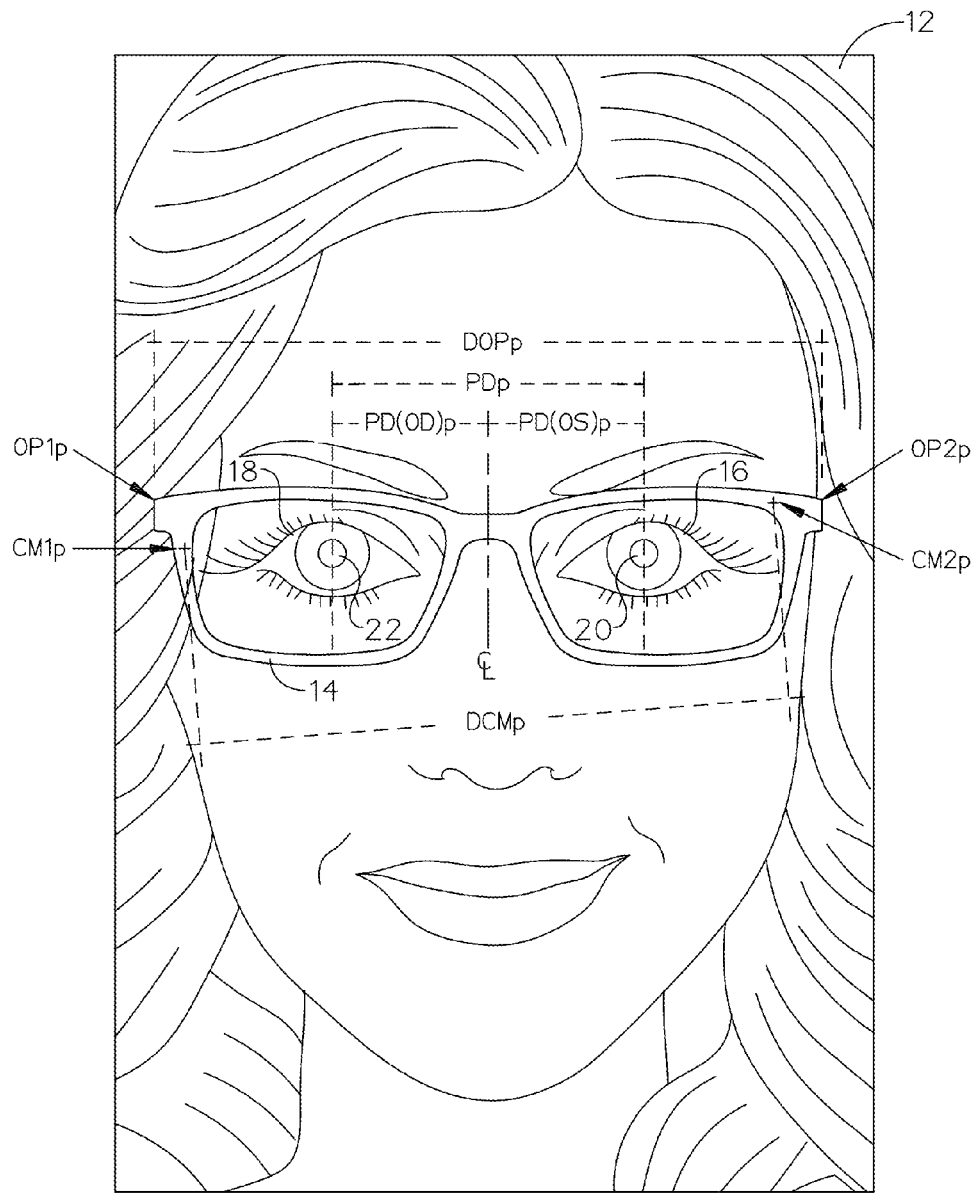
FIG. 2 is a schematic view of an exemplary embodiment of a photographed image of the present invention.
Figure 3:
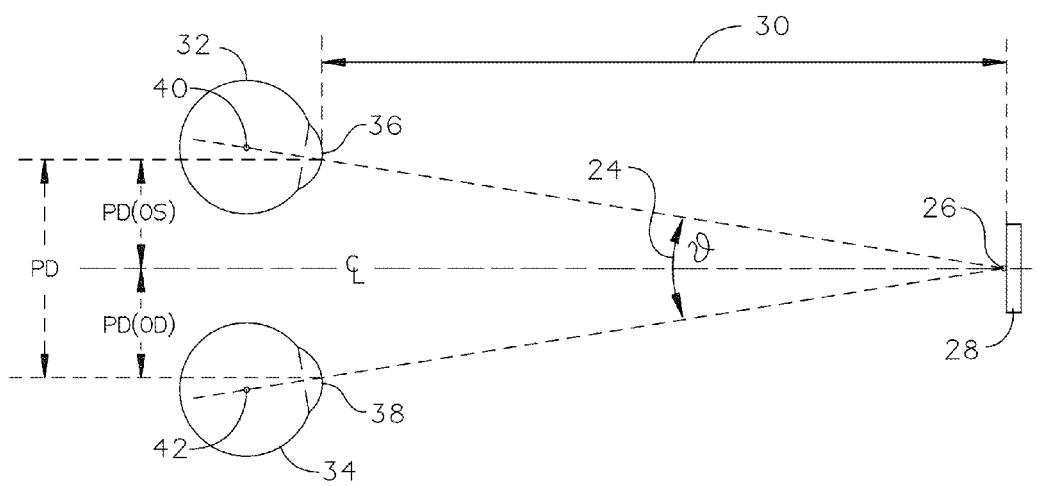
FIG. 3 is a schematic view of an exemplary embodiment of a method of measuring pupillary distance based in part on an instructed predetermined distance.

It is understood that the actual prescription distance and the instructed predetermined distance 30 between the lens 26 and the individual's left and right eye 32, 34 may be different. As long as the instructed predetermined distance 30 is known, the horizontal measurements from the centers of the eye pupils 36, 38 to the center of the nose-bridge, PD(OD), PD(OS), and PD can be sufficiently determined for the actual prescription distance base on known geometry principles of a vergence angle 24 as illustrated in FIG. 3, and an understanding that most human eyes after 4 years old have roughly the same diameter-size. This similar diameter and rotational point location allows using a vergence method and adjust the above pupillary distances in order to determine the new position of the eye pupils 36, 38 related to the rotational points 40, 42 and the vergence angle 24 corresponding to the actual prescription distance instead of the instructed predetermined distance, as illustrated in FIG. 3. For example, if the individual needs a frame for reading, the actual prescription distance may be 18 inches, and so if the photographed image 12 is taken from an instructed predetermined distance 30 of thirty-six inches, then the corresponding vergence angle 24 may be applied to adjust the calculations for the actual prescription distance of eighteen inches reading distance. On the other hand, if the individual needs a frame for driving, the focal distance is almost infinite; therefore the vergence method allows adjusting the actual prescription distance for an infinite distance from the instructed predetermined distance 30 of thirty-six inches. In certain embodiments, the above-mentioned method of accounting for a discrepancy between the instructed predetermined distance and the prescription distance is called the vergence angle methodology.

In step 74, the calculated pupillary distances of the individual are used to cut and mount the prescription lenses for a frame in alignment with their corresponding eye pupils. And then the vendor may deliver a frame with prescription lenses that may take into account relevant position of the person's nose-bridge. For remote buyers the method applies as well, wherein the individual may have never left their residence throughout the process. The above calculations may be adjusted according the lens wrap-angle of the desired frame in order to translate the pupillary distances onto the surface of the front of the individual's desired frame.

The computer-based data processing system and method described above is for purposes of example only, and may be implemented in any type of computer system or programming or processing environment, or in a computer program, alone or in conjunction with hardware. The present invention may also be implemented in software stored on a computer-readable medium and executed as a computer program on a general purpose or special purpose computer. For clarity, only those aspects of the system germane to the invention are described, and product details well known in the art are omitted. For the same reason, the computer hardware is not described in further detail. It should thus be understood that the invention is not limited to any specific computer language, program, or computer. It is further contemplated that the present invention may be run on a stand-alone computer system, or may be run from a server computer system that can be accessed by a plurality of client computer systems interconnected over an intranet network, or that is accessible to clients over the Internet. In addition, many embodiments of the present invention have application to a wide range of industries. To the extent the present application discloses a system, the method implemented by that system, as well as software stored on a computer-readable medium and executed as a computer program to perform the method on a general purpose or special purpose computer, are within the scope of the present invention. Further, to the extent the present application discloses a method, a system of apparatuses configured to implement the method are within the scope of the present invention.

It should be understood, of course, that the foregoing relates to exemplary embodiments of the invention and that modifications may be made without departing from the spirit and scope of the invention as set forth in the following claims.

What is claimed is:

1. A method for measuring pupillary distances, the method adapted to take into account a relevant position of an individual's nose-bridge, comprising:
    providing a calibration frame with at least one known measurement between two identified points, wherein the calibration frame comprises two eye-frames joined at a nose-bridge;
    capturing a photographed image of the calibration frame being comfortably worn by the individual;
    determining a scale factor of the photographed image by comparing the at least one known measurement to an apparent distance between the two identified points captured on the photographed image; and
    calculating left and right pupillary distances by multiplying the scale factor by an apparent horizontal distance between each eye-pupil and the center of the individual's nose-bridge the captured on the photographed image.

2. The method of claim 1, further comprising calculating an inter-pupillary distance by multiplying the scale factor by an apparent horizontal distance between the centers of the individual's eye-pupils captured on the photographed image.

3. The method of claim 1, further comprising capturing the photographed image from an instructed predetermined distance from the individual's left and right eyes.

4. The method of claim 1, further comprising the calibration frame being provided by a remote vendor.

5. The method of claim 4, further providing an instructed predetermined distance.

6. The method of claim 5, further comprising accounting for when the actual prescription distance differs from the instructed predetermined distance by using a vergence angle methodology.

7. The method of claim 1, wherein the two identified points of a known measurement are calibration marks disposed on the calibration frame.

8. The method of claim 1, wherein the calibration frame is disposable.

9. A system for measuring pupillary distances, the system adapted to take into account a relevant position of an individual's nose-bridge, comprising:
    a calibration frame with at least one known measurement between at least two identified points, wherein the calibration frame comprises two eye-frames joined at a nose-bridge;
    a computer having a user interface; and
    a program product comprising machine-readable program code for causing, when executed, the computer to perform the following process steps:
        instructing the user to capture and transmit a photographed image of the calibration frame being comfortably worn by the individual;
        receiving the photographed image from the user;
        determining a scale factor of the photographed image by comparing the at least one known measurement to an apparent distance between the two identified points captured on the photographed image; and
        calculating left and right pupillary distances by multiplying the scale factor by an apparent horizontal distance between each eye-pupil and the center of the individual's nose-bridge captured on the photographed image.

10. The system of claim 9, wherein the instructions further comprises calculating an interpupillary distance by multiplying the scale factor by an apparent horizontal distance between the centers of the individual's eye-pupils captured on the photographed image.

11. The system of claim 9, wherein the instructions further comprises a predetermined distance for capturing the photographed image.

12. The system of claim 11, further comprising prompting the user for an actual prescription distance, wherein a difference between the actual prescription distances and the instructed predetermined distance is accounted for by using a vergence angle methodology.

13. The system of claim 9, wherein an imaging device for capturing the photographed image is electronically connected to the program product.

14. The system of claim 9, wherein the at least two identified points are two calibration marks.

* * * * *